(12) United States Patent
Duffy et al.

(10) Patent No.: US 6,875,786 B2
(45) Date of Patent: Apr. 5, 2005

(54) THROMBOPOIETIN MIMETICS

(75) Inventors: Kevin J. Duffy, Collegeville, PA (US); Juan I. Luengo, Collegeville, PA (US); Antony N. Shaw, Collegeville, PA (US)

(73) Assignee: SmithKline Beecham Corporation, Philadelphia, PA (US)

( * ) Notice: Subject to any disclaimer, the term of this patent is extended or adjusted under 35 U.S.C. 154(b) by 27 days.

(21) Appl. No.: 10/469,365

(22) PCT Filed: Mar. 1, 2002

(86) PCT No.: PCT/US02/06259

§ 371 (c)(1), (2), (4) Date: Aug. 28, 2003

(87) PCT Pub. No.: WO02/085343

PCT Pub. Date: Oct. 31, 2002

(65) Prior Publication Data

US 2004/0077855 A1 Apr. 22, 2004

Related U.S. Application Data

(60) Provisional application No. 60/269,985, filed on Mar. 1, 2001.

(51) Int. Cl.[7] .................. A61K 31/415; C07D 231/06; C07D 257/04
(52) U.S. Cl. ................. 514/381; 514/403; 548/250; 548/370.1; 562/405
(58) Field of Search .............................. 514/381, 403; 548/250, 370.1; 562/405

(56) References Cited

U.S. PATENT DOCUMENTS

| | | | |
|---|---|---|---|
| 851,444 A | 4/1907 | Shulthess | |
| 4,435,417 A | 3/1984 | Toja et al. | |
| 4,510,149 A | 4/1985 | Cozzi et al. | |
| 4,880,788 A | 11/1989 | Moake et al. | |
| 5,482,546 A | 1/1996 | Eida | |
| 6,214,813 B1 | 4/2001 | Zhang et al. | |

FOREIGN PATENT DOCUMENTS

| | | |
|---|---|---|
| DE | 193350 | 12/1907 |
| EP | 1 207 155 | 7/2000 |
| EP | 1 253 142 | 1/2001 |
| EP | 1 104 674 | 6/2001 |
| GB | 779 880 | 7/1957 |
| WO | WO 98/46606 | 10/1998 |
| WO | WO 01/77080 | 1/2001 |
| WO | WO 02/059099 | 1/2002 |
| WO | WO 02/059100 | 1/2002 |
| WO | WO 02/38549 | 5/2002 |

OTHER PUBLICATIONS

A. Esteve, Ann. Pharm. Franc., 1950, vol. 8, No. 9–10, pp. 594–604.
Morris, et al., Anti–Cancer Drugs, 1997, vol. 8, No. 8, pp. 746–755.
Duffy, et al., J. Med. Chem., 2001, vol. 44, No. 22, Abstract No. XP002197261.
Bartley, et al., Cell, 1994, vol. 77, pp. 1117–1124.
Database CAPLUS, Yamazaki, et al., 1995, 122: 30087.
Database CAPLUS, Olszewski, et al., 1995, 122: 81695t.

*Primary Examiner*—Taofiq Solola
(74) *Attorney, Agent, or Firm*—Wayne J. Dustman; Stephen Venetianer; Charles M. Kinzig

(57) ABSTRACT

Invented are non-peptide TPO mimetics. Also invented is a method of treating thrombocytopenia, in a mammal, including a human, in need thereof which comprises administering to such mammal an effective amount of a selected hydroxy-1-azobenzene derivative.

10 Claims, No Drawings

THROMBOPOIETIN MIMETICS

This Appln is a 371 of PCT/US02/06259, filed Mar. 1, 2002 which claims the benefit of 60/269,985 filed Mar. 1, 2002.

FIELD OF THE INVENTION

This invention relates to thrombopoietin (TPO) mimetics and their use as promoters of thrombopoiesis and megakaryocytopoiesis.

BACKGROUND OF THE INVENTION

Megakaryocytes are bone marrow-derived cells, which are responsible for producing circulating blood platelets. Although comprising <0.25% of the bone marrow cells in most species, they have >10 times the volume of typical marrow cells. See Kuter et al. *Proc. Natl. Acad. Aci. USA* 91: 11104–11108 (1994). Megakaryocytes undergo a process known as endomitosis whereby they replicate their nuclei but fail to undergo cell division and thereby give rise to polypoid cells. In response to a decreased platelet count, the endomitotic rate increases, higher ploidy megakaryocytes are formed, and the number of megakaryocytes may increase up to 3-fold. See Harker *J. Clin. Invest.* 47:458–465 (1968). In contrast, in response to an elevated platelet count, the endomitotic rate decreases, lower ploidy megakaryocytes are formed, and the number of megakaryocytes may decrease by 50%.

The exact physiological feedback mechanism by which the mass of circulating platelets regulates the endomitrotic rate and number of bone marrow megakaryocytes is not known. The circulating thrombopoietic factor involved in mediating this feedback loop is now thought to be thrombopoietin (TPO). More specifically, TPO has been shown to be the main humoral regulator in situations involving thrombocytopenia. See, e.g., Metcalf Nature 369:519–520 (1994). TPO has been shown in several studies to increase platelet counts, increase platelet size, and increase isotope incorporation into platelets of recipient animals. Specifically, TPO is thought to affect megakaryocytopoiesis in several ways: (1) it produces increases in megakaryocyte size and number; (2) it produces an increase in DNA content, in the form of polyploidy, in megakaryocytes; (3) it increases megakaryocyte endomitosis; (4) it produces increased maturation of megakaryocytes; and (5) it produces an increase in the percentage of precursor cells, in the form of small acetylcholinesterase-positive cells, in the bone marrow.

Because platelets (thrombocytes) are necessary for blood clotting and when their numbers are very low a patient is at risk of death from catastrophic hemorrhage, TPO has potential useful application in both the diagnosis and the treatment of various hematological disorders, for example, diseases primarily due to platelet defects. Ongoing clinical trials with TPO have indicated that TPO can be administered safely to patients. In addition, recent studies have provided a basis for the projection of efficacy of TPO therapy in the treatment of thrombocytopenia, and particularly thrombocytopenia resulting from chemotherapy, radiation therapy, or bone marrow transplantation as treatment for cancer or lymphoma. See e.g., McDonald (1992) *Am. J. Ped. Hematology/Oncology* 14: 8–21 (1992).

The gene encoding TPO has been cloned and characterized. See Kuter et al., *Proc. Natl. Acad. Sci. USA* 91: 11104–11108 (1994); Barley et al., *Cell* 77: 1117–1124 (1994); Kaushansky et al., *Nature* 369:568–571 (1994); Wendling et al., *Nature* 369: 571–574 (1994); and Sauvage et al., *Nature* 369: 533–538 (1994). Thrombopoietin is a glycoprotein with at least two forms, with apparent molecular masses of 25 kDa and 31 kDa, with a common N-terminal amino acid sequence. See, Bartley, et al., *Cell* 77: 1117–1124 (1994). Thrombopoietin appears to have two distinct regions separated by a potential Arg-Arg cleavage site. The amino-terminal region is highly conserved in man and mouse, and has some homology with erythropoietin and interferon-a and interferon-b. The carboxy-terminal region shows wide species divergence.

The DNA sequences and encoded peptide sequences for human TPO receptor (TPO-R; also known as c-mpl) have been described. See, Vigon et al. *Proc. Natl. Acad. Sci. USA* 89: 5640–5644 (1992). TPO-R is a member of the haematopoietin growth factor receptor family, a family characterized by a common structural design of the extracellular domain, including for conserved C residues in the N-terminal portion and a WSXWS motif close to the transmembrane region. See Bazan *Proc. Natl. Acad. Sci. USA* 87: 6934–6938 (1990). Evidence that this receptor plays a functional role in hematopoiesis includes observations that its expression if restricted to spleen, bone marrow, or fetal liver in mice (see Souyri et al. *Cell* 63: 1137–1147 (1990)) and to megakaryocytes, platelets, and $CD34^+$ cells in humans (see Methia et al. *Blood* 82: 1395–1401 (1993)). Further evidence for TPOR as a key regulator of megakaryopoiesis is the fact that exposure of $CD34^+$ cells to synthetic oligonucleotides antisense to TPOR RNA significantly inhibits the appearance of megakaryocyte colonies without affecting erythroid or myeloid colony formation. Some workers postulate that the receptor functions as a homodimer, similar to the situation with the receptors for G-CSF and erythropoietin.

The slow recovery of platelet levels in patients suffering from thrombocytopenia is a serious problem, and has lent urgency to the search for a blood growth factor agonist able to accelerate platelet regeneration.

It would be desirable to provide compounds which allow for the treatment of thrombocytopenia by acting as a TPO mimetic.

As disclosed herein it has unexpectedly been discovered that certain hydroxy-1-azo-benzene derivatives are effective as agonists of the TPO receptor, they are potent TPO mimetics.

SUMMARY OF THE INVENTION

This invention relates to compounds of Formula (I):

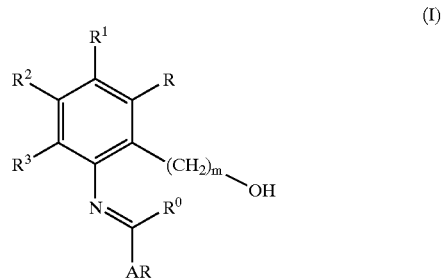

(I)

wherein:
R, $R^1$, $R^2$ and $R^3$ are each independently selected from hydrogen, $C_{1-6}$alkyl, $—(CH_2)_pOR^4$, $—C(O)OR^4$, formyl, nitro, cyano, halogen, aryl, substituted aryl, substituted alkyl, $—S(O)_nR^4$, cycloalkyl, $—NR^5R^6$, protected $—OH$, $—CONR^5R^6$, phosphonic acid, sulfonic acid, phosphinic acid and $—SO_2NR^5R^6$, where
p is 0–6,
n is 0–2,
$R^4$ is hydrogen, alkyl, cycloalkyl, $C_1$–$C_{12}$aryl, substituted alkyl, substituted cycloalkyl and substituted $C_1$–$C_{12}$aryl, and
$R^5$ and $R^6$ are each independently selected from hydrogen, alkyl, substituted alkyl, $C_{3-6}$cycloalkyl, and aryl,
or $R^5$ and $R^6$ taken together with the nitrogen to which they are attached represent a 5 to 6 member saturated ring containing up to one other heteroatom selected from oxygen and nitrogen;
$R^0$ is selected from hydrogen, $C_1$–$C_{10}$alkyl and substituted $C_1$–$C_{10}$ alkyl;
m is 0–6; and
AR is a cyclic or polycyclic aromatic ring containing from 3 to 16 carbon atoms and optionally containing one or more heteroatoms, provided that when the number of carbon atoms is 3 the aromatic ring contains at least two heteroatoms and when the number of carbon atoms is 4 the aromatic ring contains at least one heteroatom, and optionally substituted with one or more substituents selected from the group consisting of: alkyl, substituted alkyl, aryl, substituted cycloalkyl, substituted aryl, aryloxy, oxo, hydroxy, alkoxy, cycloalkyl, acyloxy, amino, N-acylamino, nitro, cyano, halogen, —C(O)OR$^4$, —C(O)NR$^{10}$R$^{11}$, —S(O)$_2$NR$^{10}$R$^{11}$, —S(O)$_n$R$^4$ and protected —OH,
where n is 0–2,
$R^4$ is hydrogen, alkyl, cycloalkyl, $C_1$–$C_{12}$aryl, substituted alkyl, substituted cycloalkyl and substituted $C_1$–$C_{12}$aryl; and
$R^{10}$ and $R^{11}$ are independently hydrogen, cycloalkyl, $C_1$–$C_{12}$aryl, substituted cycloalkyl, substituted $C_1$–$C_{12}$aryl, alkyl or alkyl substituted with one or more substituents selected from the group consisting of: alkoxy, acyloxy, aryloxy, amino, N-acylamino, oxo, hydroxy, —C(O)OR$^4$, —S(O)$_n$R$^4$, —C(O)NR$^4$R$^4$, S(O)$_2$NR$^4$R$^4$, nitro, cyano, cycloalkyl, substituted cycloalkyl, halogen, aryl, substituted aryl and protected —OH,
or $R^{10}$ and $R^{11}$ taken together with the nitrogen to which they are attached represent a 5 to 6 member saturated ring containing up to one other heteroatom selected from oxygen and nitrogen,
where $R^4$ is as described above and n is 0–2;
and pharmaceutically acceptable salts, hydrates, solvates and esters thereof;
provided that at least one of R, $R^1$, $R^2$ and $R^3$ is a substituted aryl group.

This invention relates to a method of treating thrombocytopenia, which comprises administering to a subject in need thereof an effective amount of a TPO mimetic compound of Formula (I).

The present invention also relates to the discovery that the compounds of Formula (I) are active as agonists of the TPO receptor.

In a further aspect of the invention there is provided novel processes and novel intermediates useful in preparing the presently invented TPO mimetic compounds.

Included in the present invention are pharmaceutical compositions comprising a pharmaceutical carrier and compounds useful in the methods of the invention.

Also included in the present invention are methods of co-administering the presently invented TPO mimetic compounds with further active ingredients.

DETAILED DESCRIPTION OF THE INVENTION

This invention relates to compounds of Formula (I) as described above.

Preferred among the presently invented compounds of Formula (I) are those having Formula (II):

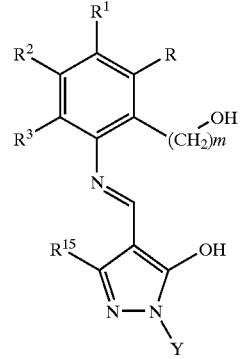

(II)

wherein:
R, $R^1$, $R^2$ and $R^3$ are each independently selected from hydrogen, $C_{1-6}$alkyl, —(CH$_2$)$_p$OR$^4$, —C(O)OR$^4$, formyl, nitro, cyano, halogen, aryl, substituted aryl, substituted alkyl, —S(O)$_n$R$^4$, cycloalkyl, —NR$^5$R$^6$, protected —OH, —CONR$^5$R$^6$, phosphonic acid, sulfonic acid, phosphinic acid and —SO$_2$NR$^5$R$^6$,
where
p is 0–6,
n is 0–2,
$R^4$ is hydrogen, alkyl, cycloalkyl, $C_1$–$C_{12}$aryl, substituted alkyl, substituted cycloalkyl and substituted $C_1$–$C_{12}$aryl, and
$R^5$ and $R^6$ are each independently selected from hydrogen, alkyl, substituted alkyl, $C_{3-6}$cycloalkyl, and aryl,
or $R^5$ and $R^6$ taken together with the nitrogen to which they are attached represent a 5 to 6 member saturated ring containing up to one other heteroatom selected from oxygen and nitrogen;
$R^{15}$ is selected from the group consisting of alkyl, $C_1$–$C_{12}$aryl, hydroxy, substituted alkyl, substituted $C_1$–$C_{12}$aryl and halogen;
m is 0–6; and
Y is selected from alkyl, substituted alkyl and a cyclic or polycyclic aromatic ring containing from 3 to 14 carbon atoms and optionally containing from one to three heteroatoms, provided that when the number of carbon atoms is 3 the aromatic ring contains at least two heteroatoms and when the number of carbon atoms is 4 the aromatic ring contains at least one heteroatom, and optionally substituted with one or more substituents selected from the group consisting of: alkyl, substituted alkyl, $C_1$–$C_{12}$aryl, substituted cycloalkyl, substituted $C_1$–$C_{12}$aryl, hydroxy, aryloxy, alkoxy, cycloalkyl, nitro, cyano, halogen and protected —OH and pharmaceutically acceptable salts, hydrates, solvates and esters thereof;
provided that at least one of R, $R^1$, $R^2$ and $R^3$ is a substituted aryl group.

Preferred among the presently invented Formula II compounds are those in which, either:
R is a substituted aryl; and $R^1$ is hydrogen;

or:

R is hydrogen; and $R^1$ is a substituted aryl;
and in either case:

$R^2$ and $R^3$ are each independently selected from hydrogen, $C_{1-6}$alkyl, $C_{1-6}$oxy, nitro, cyano, halogen, aryl, substituted aryl, substituted alkyl, cycloalkyl, phosphonic acid, phosphinic acid and sulfonic acid;

$R^{15}$ is selected from the group consisting of alkyl, substituted alkyl, $C_1-C_{12}$aryl, alkoxy and halogen;

m is 0–4; and

Y is selected from, phenyl, pyridinyl and pyrimidinyl, where the phenyl, pyridinyl and pyrimidinyl are optionally substituted with from one to three substituents selected from the group consisting of: alkyl, substituted alkyl, $C_1-C_{12}$aryl, substituted $C_1-C_{12}$aryl, alkoxy and halogen;

and pharmaceutically acceptable salts, hydrates, solvates and esters thereof.

Particularly preferred among the presently invented Formula II compounds are those in which, R is a substituted $C_1-C_{12}$aryl;
and $R^1$ is hydrogen;

$R^2$ and $R^3$ are each independently selected from hydrogen, $C_{1-6}$alkyl, $C_{1-6}$alkoxy, nitro, cyano, halogen, substituted alkyl and cycloalkyl;

$R^{15}$ is selected from the group consisting of alkyl, substituted alkyl, $C_1-C_{12}$aryl, alkoxy and halogen;

m is 0–2; and

Y is selected from, phenyl, pyridinyl and pyrimidinyl, where the phenyl, pyridinyl and pyrimidinyl are optionally substituted with from one to three substituents selected from the group consisting of: alkyl, substituted alkyl, $C_1-C_{12}$aryl, substituted $C_1-C_{12}$aryl, alkoxy and halogen;

and pharmaceutically acceptable salts, hydrates, solvates and esters thereof.

The most preferred among the presently invented Formula II compounds are those in which:

R is a substituted phenyl or pyridinyl ring; and $R^1$ is hydrogen;

$R^2$ and $R^3$ are each independently selected from hydrogen, $C_{1-6}$alkyl, substituted alkyl and halogen;

$R^{15}$ is selected from the group consisting of $C_{1-4}$alkyl, $C_{1-4}$alkoxy, $C_1-C_{12}$aryl and halogen;

m is 0; and

Y is selected from, phenyl, pyridinyl and pyrimidinyl, where the or phenyl, pyridinyl and pyrimidinyl is optionally substituted with one to three substituents selected from the group consisting of: alkyl, substituted alkyl, $C_1-C_{12}$aryl, substituted $C_1-C_{12}$aryl, alkoxy and halogen;

and pharmaceutically acceptable salts, hydrates, solvates and esters thereof.

Preferred among the presently invented compounds is 3'-{[1-(3,4-Dimethylphenyl)3-methyl-5-oxo-1,5-dihydropyrazol-4-ylidenemethyl]amino}-2'-hydroxybiphenyl-3-carboxylic acid;
and pharmaceutically acceptable salts, hydrates, solvates and esters thereof.

Compounds of Formula (I) are included in the pharmaceutical compositions of the invention and used in the methods of the invention.

By the term "protected hydroxy" or "protected —OH" as used herein, is meant the alcoholic or carboxylic-OH groups which can be protected by conventional blocking groups in the art such as described in "Protective Groups In Organic Synthesis" by Theodora W. Greene, Wiley-Interscience, 1981, New York. Compounds containing protected hydroxy groups may also be useful as intermediates in the preparation of the pharmaceutically active compounds of the invention.

By the term "aryl" as used herein, unless otherwise defined, is meant a cyclic or polycyclic aromatic ring containing from 1 to 14 carbon atoms and optionally containing from one to five heteroatoms, provided that when the number of carbon atoms is 1 the aromatic ring contains at least four heteroatoms, when the number of carbon atoms is 2 the aromatic ring contains at least three heteroatoms, when the number of carbons is 3 the aromatic ring contains at least two heteroatoms and when the number of carbon atoms is 4 the aromatic ring contains at least one heteroatom.

By the term "$C_1-C_{12}$aryl" as used herein, unless otherwise defined, is meant phenyl, naphthalene, 3,4-methylenedioxyphenyl, pyridine, biphenyl, quinoline, pyrimidine, quinazoline, thiophene, furan, pyrrole, pyrazole, imidazole and tetrazole.

By the term "substituted" as used herein, unless otherwise defined, is meant that the subject chemical moiety has one or more substituents selected from the group consisting of: —$CO_2R^{20}$, aryl, —$C(O)NHS(O)_2R^{20}$, —$NHS(O)_2R^{20}$, hydroxyalkyl, alkoxy, —$C(O)NR^{21}R^{22}$, acyloxy, alkyl, amino, N-acylamino, hydroxy, —$(CH_2)_gC(O)OR^8$, —$S(O)_n R^8$, nitro, tetrazole, cyano, oxo, halogen, trifluoromethyl and protected —OH, where g is 0–6, $R^8$ is hydrogen or alkyl, $R^{20}$ is selected form hydrogen, $C_1-C_4$alkyl, aryl and trifluoromethyl, and $R^{21}$ and $R^{22}$ are independently selected form hydrogen, $C_1-C_4$alkyl, aryl and trifluoromethyl, and n is 0–2.

By the term "alkoxy" as used herein is meant —Oalkyl where alkyl is as described herein including —$OCH_3$ and —$OC(CH_3)_2CH_3$.

The term "cycloalkyl" as used herein unless otherwise defined, is meant a nonaromatic, unsaturated or saturated, cyclic or polycyclic $C_3-C_{12}$.

Examples of cycloalkyl and substituted cycloalkyl substituents as used herein include: cyclohexyl, 4-hydroxycyclohexyl, 2-ethylcyclohexyl, propyl 4-methoxycyclohexyl, 4-methoxycyclohexyl, 4-carboxycyclohexyl, cyclopropyl and cyclopentyl.

By the term "acyloxy" as used herein is meant —OC(O)alkyl where alkyl is as described herein. Examples of acyloxy substituents as used herein include: —$OC(O)CH_3$, —$OC(O)CH(CH_3)_2$ and —$OC(O)(CH_2)_3CH_3$.

By the term "N-acylamino" as used herein is meant —N(H)C(O)alkyl, where alkyl is as described herein. Examples of N-acylamino substituents as used herein include: —$N(H)C(O)CH_3$, —$N(H)C(O)CH(CH_3)_2$ and —$N(H)C(O)(CH_2)_3CH_3$.

By the term "aryloxy" as used herein is meant -Oaryl where aryl is phenyl, naphthyl, 3,4-methylenedioxyphenyl, pyridyl or biphenyl optionally substituted with one or more substituents selected from the group consisting of: alkyl, hydroxyalkyl, alkoxy, trifuloromethyl, acyloxy, amino, N-acylamino, hydroxy, —$(CH_2)_gC(O)OR^8$, —$S(O)_n R^8$, nitro, cyano, halogen and protected —OH, where g is 0–6, $R^8$ is hydrogen or alkyl, and n is 0–2. Examples of aryloxy substituents as used herein include: phenoxy, 4-fluorophenyloxy and biphenyloxy.

By the term "heteroatom" as used herein is meant oxygen, nitrogen or sulfur.

By the term "halogen" as used herein is meant a substituent selected from bromide, iodide, chloride and fluoride.

By the term "alkyl" and derivatives thereof and in all carbon chains as used herein is meant a linear or branched, saturated or unsaturated hydrocarbon chain, and unless otherwise defined, the carbon chain will contain from 1 to 12 carbon atoms. Examples of alkyl substituents as used herein include: —$CH_3$, —$CH_2$—$CH_3$, —$CH_2$—$CH_2$—$CH_3$, —$CH(CH_3)_2$, —$C(CH_3)_3$, —$(CH_2)_3$—$CH_3$, —$CH_2$—$CH(CH_3)_2$, —$CH(CH_3)$—$CH_2$—$CH_3$, —$CH=CH_2$, and —$C\equiv C$—$CH_3$.

By the term "treating" and derivatives thereof as used herein, is meant prophylatic and therapeutic therapy.

All publications, including but not limited to patents and patent applications, cited in this specification are herein incorporated by reference as though fully set forth.

Compounds of Formula (I) are included in the pharmaceutical compositions of the invention and used in the methods of the invention. Where a —COOH or —OH group is present, pharmaceutically acceptable esters can be employed, for example methyl, ethyl, pivaloyloxymethyl, and the like for —COOH, and acetate maleate and the like for —OH, and those esters known in the art for modifying solubility or hydrolysis characteristics, for use as sustained release or prodrug formulations.

The novel compounds of Formulas I and II are prepared as shown in Schemes I to IV below, or by analogous methods, wherein the 'R' substituents, AR, Y and m are as defined in Formulas I and II respectively and provided that the 'R' and m substituents, AR and Y do not include any such substituents that render inoperative the processes of Schemes I to IV. All of the starting materials are commercially available or are readily made from commercially available starting materials by those of skill in the art.

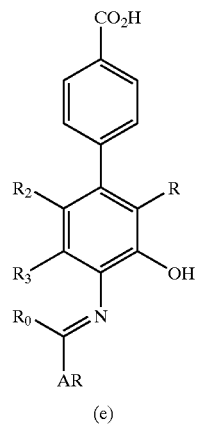

i), nitric acid, sulfuric acid; ii) 4-carboxyphenylboronic acid, Pd(PPh$_3$)$_4$, Na2CO3, dioxane, water; iii) H$_2$, Pd—C; iv) ARCOR, NaOAc, water, EtOH.

Scheme I outlines the formation of Formula I compounds. As used in scheme I, a 3-bromophenol (a) is nitrated with nitric acid or sodium nitrate and sulfuric acid to give nitro phenol (b). Coupling of (b) with a substituted arylboropic acid such as 3-carboxyphenylboronic acid or 4-carboxyphenylboronic acid in the presence of a catalyst, preferably tetrakistriphenylphosphino palladium and a base such as sodium carbonate ot triethylamine in a suitable solvent such as aqueous 1,4-dioxane or dimethylformamide afforded substituted aryl compound (c). Reduction of the nitro group by catalytic hydrogenation or mediated by a reducing metal such as iron of tin dichloride in a suitable solvent such as ethanol, acetic acid or water gives the aniline (d) Compound (d) is reacted with an aldehyde or ketone in aqueous ethanol preferably in the presence of sodium acetate to give the final product (e).

Scheme I

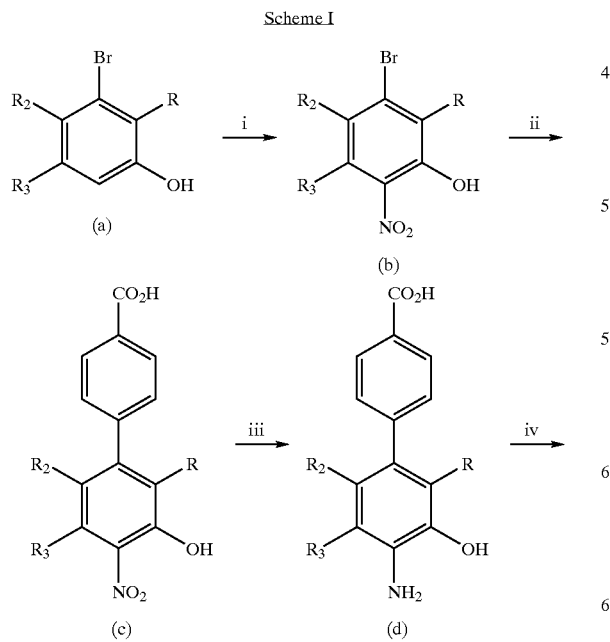

Scheme II

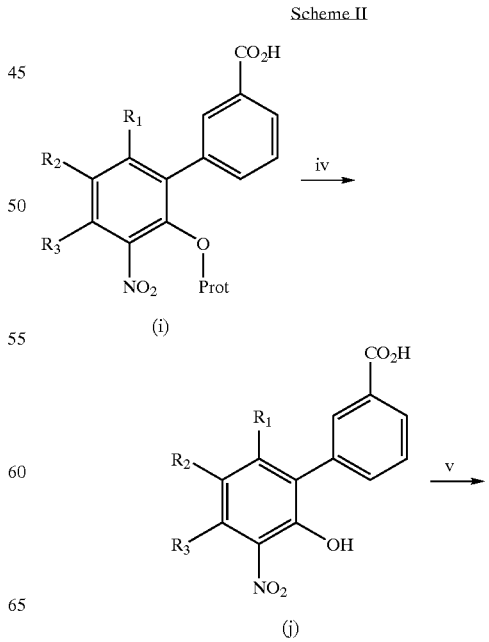

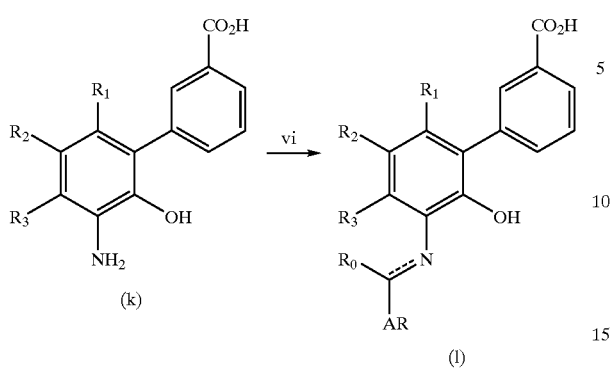

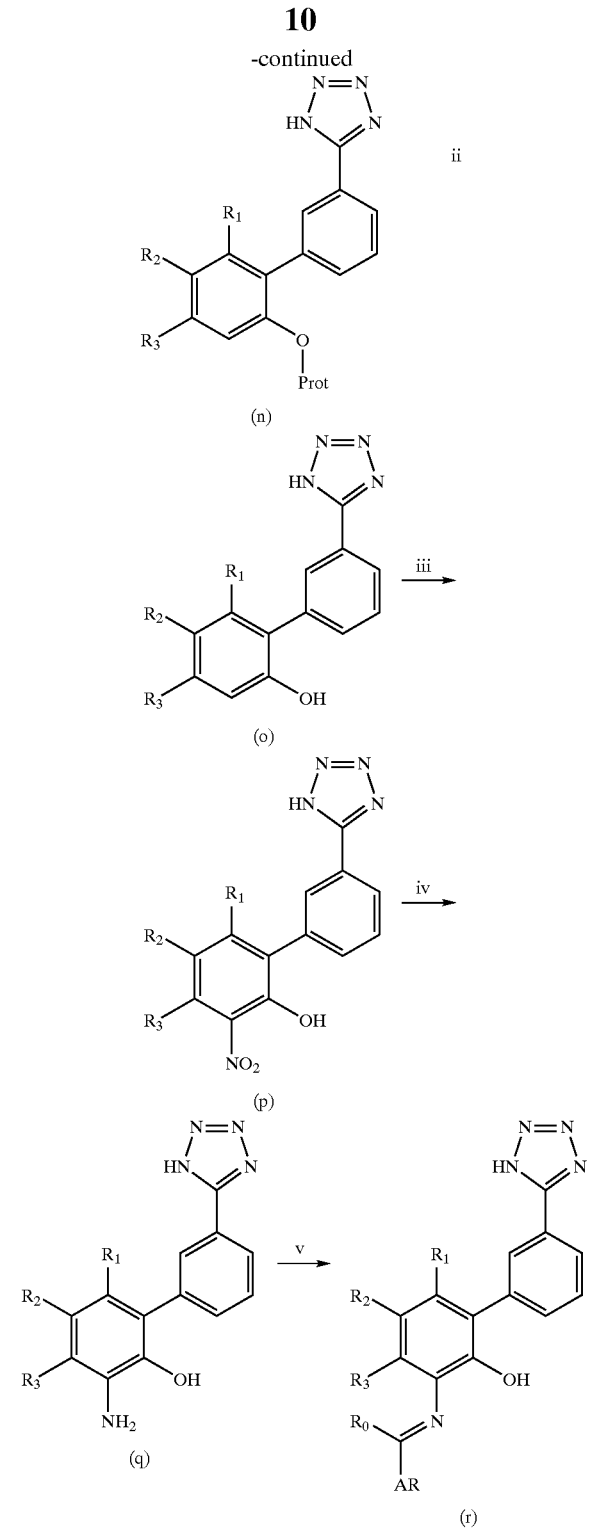

i), NaNO₂, sulfuric acid; ii), MeI, K₂CO₃, acetone; iii) 3-carboxyphenylboronic acid, Pd(PPh₃)₄, Na2CO3, dioxane, water; iv) 48% aqu. HBr, AcOH; v) H₂, Pd—C; vi) ARCOR, NaOAc, water, EtOH.

Scheme II outlines an alternative synthesis of Formula I compounds. A 2-bromophenol (f) (such as 2-bromoanisole or 2-bromo-5-methylanisole is nitrated with nitric acid or sodium nitrate and sulfuric acid to give nitro compound (g). The phenol (g) is then protected by reaction with an alkylating agent such as benzyl bromide or preferably methyl iodide in the presence of a base such as sodium hydride or potassium carbonate in a suitable solvent such as dimethylformamide, tetrahydrofuran or acetone to give protected nitrophenol (h) (Prot=alkyl or substituted alkyl, e.g. methyl, benzyl). Coupling of (h) with a substituted arylboronic acid such as 3-carboxyphenylboronic acid or 4-carboxyphenylboronic acid in the presence of a catalyst, preferably tetrakistriphenylphosphino palladium and a base such as sodium carbonate ot triethylamine in a suitable solvent such as aqueous 1,4-dioxane or dimethylformamide afforded substituted aryl compound (i). Removal of the protecting group (Prot) is accomplished using an protic or Lewis acid such as concentrated hydrobromic acid, boron tribromide or trimethylsilyl iodide to affored the phenol (j). Reduction of the nitro group by catalytic hydrogenation or mediated by a reducing metal such as iron of tin dichloride in a suitable solvent such as ethanol, acetic acid or water gives the aniline (k) Compound (k) is reacted with an aldehyde or ketone in aqueous ethanol preferably in the presence of sodium acetate to give the final product (l).

Scheme III

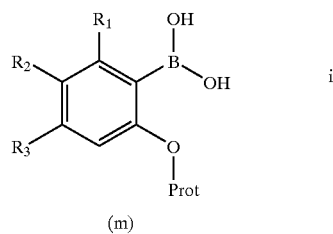

i) 5-(3-bromophenyl)tetrazole, Pd(PPh₃)₄, Na2CO3, dioxane, water; ii) 48% aqu. HBr, AcOH; iii) HNO₂, AcOH; iv) H₂, Pd—C; v) ARCOR, NaOAc, water, ETOH.

Scheme III outline a further procedure for the synthesis of Formula I compounds. A protected hydroxyphenylboronic acid (m) (Prot=alkyl or substituted alkyl, e.g. methyl, benzyl) such as 5-chloro-2-methoxyphenylboronic acid, 5-fluoro-2-methoxyphenyl; boronic acid or 2-methoxy-5- formylphenylboronic acid is coupled with a substituted halogenoaryl species such as 5-(3-bromophenyl)tetrazole or 5-bromonicotinic acid in the presence of a catalyst, preferably tetrakistriphenylphosphino palladium and a base such as sodium carbonate ot triethylamine in a suitable solvent such as aqueous 1,4-dioxane or dimethylformamide afforded substituted aryl compound (n). Removal of the protecting group Prot is accomplished using an protic or Lewis acid such as concentrated hydrobromic acid, boron tribromide or trimethylsilyl iodide to afford the phenol (O). Nitration of (O) with nitric acid or sodium nitrate in the presence of an acid such as acetic or hydrochloric acid affords the nitro compound (p). Reduction of the nitro group by catalytic hydrogenation or mediated by a reducing metal such as iron of tin dichloride in a suitable solvent such as ethanol, acetic acid or water gives the aniline (q) Compound (q) is reacted with an aldehyde or ketone in aqueous ethanol preferably in the presence of sodium acetate to give the final product (r).

Scheme IV

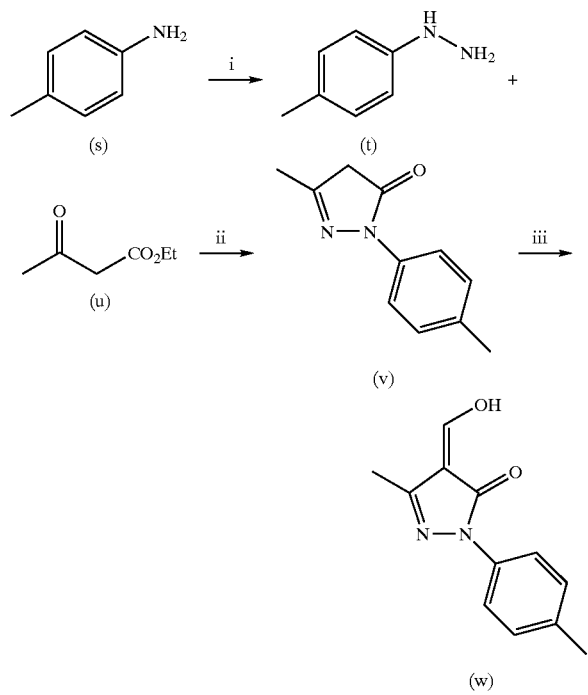

i) NaNO$_2$, HCl, water then SnCl$_2$, water; ii) AcOH, heat, iii) POCl$_3$, DMF, 0–100° C.

Scheme IV outlines the formation of pyrazoles for use in scheme I-III. An amine such as 4-methylaniline, compound (s), is diazotized by the action of sodium nitrite and an appropriate acid such as hydrochloric acid, nitric acid or sulfuric acid in an appropriate aqueous solvent system such as water or ethanol-water mixtures then reduced in situ by tin chloride to afford hydrazine, compound (t). The hydrazine is then condensed with a electrophilic carbonyl species such as ethyl acetoacetate (u), ethyl cyanoacetate or diethyl malonate, in an appropriate solvent such as acetic acid or ethanol at an appropriate temperature typically 0–100° C. to give the corresponding pyrazole, compound (v). Heating (v) with the reagent generated from phosphorus oxychloride and dimethylformamide, typically at 100° C. gives the pyrazole aldehyde (w) as described herein.

The treatment of thrombocytopenia, as described herein, is accomplished by enhancing the production of platelets.

By the term "co-administering" and derivatives thereof as used herein is meant either simultaneous administration or any manner of separate sequential administration of a TPO mimetic compound, as described herein, and a further active ingredient or ingredients, known to treat thrombocytopenia, including chemotherapy-induced thrombocytopenia and bone marrow transplantation and other conditions with depressed platelet production. Preferably, if the administration is not simultaneous, the compounds are administered in a close time proximity to each other. Furthermore, it does not matter if the compounds are administered in the same dosage form, e.g. one compound may be administered topically and another compound may be administered orally.

Because the pharmaceutically active compounds of the present invention are active as TPO mimetics they exhibit therapeutic utility in treating thrombocytopenia and other conditions with depressed platelet production.

In determining potency as TPO mimetics, the following assays are employed:

Luciferase Assay

Compounds of the present invention are tested for potency as mimetics of the TPO receptor in a Luciferase assay such as described in Lamb, et al., *Nucleic Acids Research* 23: 3283–3289 (1995) and Seidel, et al., *Proc. Natl. Acad. Sci. USA* 92: 3041–3045 (1995) by substituting a TPO-responsive BaF3 cell line (Vigon et al. *Proc. Natl. Acad. Sci. USA* 1992, 89, 5640–5644) for the HepG2 cells utilized therein. The murine BaF3 cells express TPO receptors and closely match the pattern of STAT (signal transducers and activators of transcription) activation observed in primary murine and human bone marrow cells.

Proliferation Assay

A compound of this invention was active in an in vitro proliferation assay using the human UT7TPO cell line. UT7TPO cells are a human megakaryoblastic cell line that express Tpo-R, whose survival and growth is dependent on the presence of TPO.

The pharmaceutically active compounds within the scope of this invention are useful as TPO mimetics in mammals, including humans, in need thereof.

The compound of Example 1, promoted the proliferation of 32D-mpl cells at a concentration of 0.03 to 30 uM. (EC$_{50}$/uM, % TPO$_{max}$ 0.67, 85%)

The present invention therefore provides a method of treating thrombocytopenia and other conditions with depressed platelet production, which comprises administering a compound of Formula (I) or a pharmaceutically acceptable salt, hydrate, solvate or ester thereof in a quantity effective to enhance platelet production. The compounds of Formula (I) also provide for a method of treating the above indicated disease states because of their demonstrated ability to act as TPO mimetics. The drug may be administered to a patient in need thereof by any conventional route of administration, including, but not limited to, intravenous, intramuscular, oral, subcutaneous, intradermal, and parenteral.

The pharmaceutically active compounds of the present invention are incorporated into convenient dosage forms such as capsules, tablets, or injectable preparations. Solid or liquid pharmaceutical carriers are employed. Solid carriers include, starch, lactose, calcium sulfate dihydrate, terra alba, sucrose, talc, gelatin, agar, pectin, acacia, magnesium stearate, and stearic acid. Liquid carriers include syrup, peanut oil, olive oil, saline, and water. Similarly, the carrier or diluent may include any prolonged release material, such as glyceryl monostearate or glyceryl distearate, alone or with a wax. The amount of solid carrier varies widely but, preferably, will be from about 25 mg to about 1 g per dosage unit. When a liquid carrier is used, the preparation will be in the form of a syrup, elixir, emulsion, soft gelatin capsule, sterile injectable liquid such as an ampoule, or an aqueous or nonaqueous liquid suspension.

The pharmaceutical preparations are made following conventional techniques of a pharmaceutical chemist involving mixing, granulating, and compressing, when necessary, for tablet forms, or mixing, filling and dissolving the ingredients, as appropriate, to give the desired oral or parenteral products.

Doses of the presently invented pharmaceutically active compounds in a pharmaceutical dosage unit as described above will be an efficacious, nontoxic quantity preferably selected from the range of 0.001–100 mg/kg of active compound, preferably 0.001–50 mg/kg. When treating a human patient in need of a TPO mimetic, the selected dose is administered preferably from 1–6 times daily, orally or parenterally. Preferred forms of parenteral administration include topically, rectally, transdermally, by injection and continuously by infusion. Oral dosage units for human administration preferably contain from 0.05 to 3500 mg of active compound. Oral administration, which uses lower dosages is preferred. Parenteral administration, at high dosages, however, also can be used when safe and convenient for the patient.

Optimal dosages to be administered may be readily determined by those skilled in the art, and will vary with the particular TPO mimetic in use, the strength of the preparation, the mode of administration, and the advancement of the disease condition. Additional factors depending on the particular patient being treated will result in a need to adjust dosages, including patient age, weight, diet, and time of administration.

The method of this invention of inducing TPO mimetic activity in mammals, including humans, comprises administering to a subject in need of such activity an effective TPO mimetic amount of a pharmaceutically active compound of the present invention.

The invention also provides for the use of a compound of Formula (I) in the manufacture of a medicament for use as a TPO mimetic.

The invention also provides for the use of a compound of Formula (I) in the manufacture of a medicament for use in therapy.

The invention also provides for the use of a compound of Formula (I) in the manufacture of a medicament for use in enhancing platelet production.

The invention also provides for the use of a compound of Formula (I) in the manufacture of a medicament for use in treating thrombocytopenia.

The invention also provides for a pharmaceutical composition for use as a TPO mimetic which comprises a compound of Formula (I) and a pharmaceutically acceptable carrier.

The invention also provides for a pharmaceutical composition for use in the treatment of thrombocytopenia which comprises a compound of Formula (I) and a pharmaceutically acceptable carrier.

The invention also provides for a pharmaceutical composition for use in enhancing platelet production which comprises a compound of Formula (I) and a pharmaceutically acceptable carrier.

No unacceptable toxicological effects are expected when compounds of the invention are administered in accordance with the present invention.

In addition, the pharmaceutically active compounds of the present invention can be co-administered with further active ingredients, such as other compounds known to treat thrombocytopenia, including chemotherapy-induced thrombocytopenia and bone marrow transplantation and other conditions with depressed platelet production, or compounds known to have utility when used in combination with a TPO mimetic.

Contemplated Equivalents—It will be appreciated by the person of ordinary skill in the art that the compounds of Formulas I and II may also exist in tautomeric forms. For example, in Formula I, the double bond that is drawn between the nitrogen atom and the carbon atom exists between the carbon atom and the AR substituent. Tautomeric forms of the compounds of Formulas I and II are exemplified by the following Formula (III):

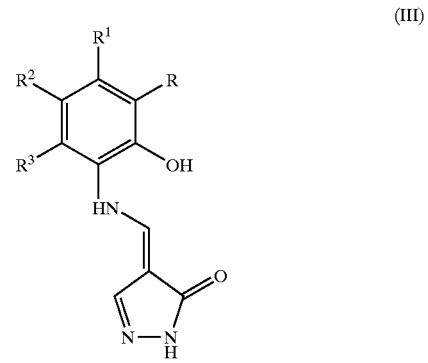

where the 'R' groups are as defined above. All such compounds are included in the scope of the invention and inherently included in the definition of the compounds of Formulas I and II.

Without further elaboration, it is believed that one skilled in the art can, using the preceding description, utilize the present invention to its fullest extent. The following Examples are, therefore, to be construed as merely illustrative and not a limitation of the scope of the present invention in any way.

EXPERIMENTAL DETAILS

Example 1

Preparation of 3'-{[1-(3,4-Dimethylphenyl)-3-methyl-5-oxo-1,5-dihydropyrazol-4-ylidenemethyl]amino}-2'-hydroxybiphenyl-3-carboxylic Acid a) 2-bromo-6-nitrophenol 2-Bromophenol (50.0 g, 0.29 mol) was added slowly to a cold (10° C.) solution of sodium nitrate (36.9 g, 0.43 mol) in conc. sulfuric acid (79 g) and water (100 mL) and the resulting mixture was allowed to stir at room temperature for 2 h. Water (400 mL) was added and the resulting mixture was extracted with diethyl ether and the extract was dried (MgSO$_4$), filtered and concentrated. The residue was purified by flash chromatography (silica gel, 5% ethyl acetate/hexane). The partly purified product was triturated with hexane to afford the title compound (19.2 g, 30%) as a bright, yellow solid. $^1$H NMR (300 MHz, CDCl) δ 11.10 (S, 1h), 8.13 (d, J=7.9 Hz, 1H), 7.89 (d, J=7.9 Hz, 1H), 6.90 (t,J=7.9 Hz, 1H).

b) 2-bromo-6-nitroanisole

A mixture of 2-bromo-6-nitrophenol (10.8 g; 0.0495 mol.), methyl iodide (3.4 mL; 0.00545 mol.) and potassium carbonate (8.2 g; 0.0592 mol.) in acetone (250 mL) was stirred and heated under reflux for 24 h.

The mixture was evaporated and the residue triturated with water to afford the title compound (8.7 g; 76%). mp 55–56° C. $^1$H NMR (300 MHz, CDCl$_3$ δ 7.81–7.74 (m, 2H), 7.13 (t, J=8.1 Hz, 1H), 4.02 (s, 3H).

c) 2'-hydroxy-3'-nitrobiphenyl-3-carboxylic Acid

A mixture of 2-bromo-nitroanisole (5.00 g, 21.5 mmol.), 3-carboxyphenylboronic acid (3.58 g, 21.5 mmol.), 2M aq. sodium carbonate (20.0 mL; 40 mmol.), tetrakistriphenylphosphino palladium(0) (800 mg, 0.69 mmol)) and 1,4-dioxane (150 mL) was stirred and heated under reflux under argon for 24 h.

The reaction mixture was cooled, evaporated under reduced pressure and the residue stirred with 2M aq. sodium hydroxide (250 mL) for 1 h. The solid was filtered and washed well with water. The filtrate was washed with diethyl ether, then acidified with conc. hydrochloric acid and extracted with ethyl acetate. The extracts were washed with water and saturated aq. sodium chloride, then dried $(MgSO)_4$ and evaporated under reduced pressure to afford the crude 2'-methoxy product.

A solution of this compound in glacial acetic acid (45.0 mL) and 48% aq. hydrobromic acid (45.0 mL) was stirred and heated under reflux for 5 h.

The mixture was cooled, filtered, washed with water and dried to afford the title compound (3.31 g; 59%) as a tan powder. $^1H$ NMR (300 MHz, $d_6$-DMSO) δ 13.90 (s, 1H), 10.66 (s, 1H), 8.12 (t, J=1.7 Hz, 1H), 8.07 (dd, J=8.4, 1.7 Hz, 1H), 7.98 (dt, 7 .8, 1.5 Hz, 1H), 7.79 (dt, J=8.1, 1.7 Hz, 1H), 7.74 (dd, J=75, 1.7 Hz, 1H), 7.62 (t, J=7.8 H z,1H), 7.17 (dd, J=8.4, 7.5 Hz, 1H).

d) 3'-amino-2'-hydroxybiphenyl-3-carboxylic Acid Hydrochloride

A suspension of 2'-hydroxy-3'-nitrobiphenyl-3-carboxylic acid (2.83 g, 10.9 mmol.) and 5% palladium on carbon (580 mg, 0.27 mmol) in methanol (20.0 mL) was stirred under hydrogen at room temperature for 2 h. The hydrogen was removed and the mixture filtered into 3M aq. hydrochloric acid (5 mL). The solvent was removed under reduced pressure to afford the title compound (2.79 g; 96%) as a brown solid. $^1H$ NMR (300 MHz, $d_6$-DMSO) δ 9.9–9.3 (br s, 2H), 8.08 (s, 1H), 7.95 (d, J=7.8 Hz, 1H), 7.74 (d, J=7.8 J=7.8 Hz, 1H), 7.34 (dd, J=7.8, 1.4 Hz, 1H), 7.24 (dd, J=7.8, 1.3 Hz, 1H), 7.04 (t, J=7.8 Hz, 1H).

e) 1-(3,4-Dimethylphenyl)-3-methyl-3-pyrazolin-5-one

A solution of 3,4-dimethylphenylhydrazine hydrochloride (17.7 g; 0.1 mol.), ethyl acetoacetate (13.0 g; 0.1 mol.) and sodium acetate (8.2 g; 0.1 mol.) in glacial acetic acid (250 mL) was stirred and heated under reflux for 24 h.

The mixture was cooled and evaporated and the residue dissolved in diethyl ether (IL) and carefully washed with sat. aq. sodium hydrogen carbonate (5×200 mL). The ethereal layer was evaporated to afford the title compound (15.4 g; 76%). $^1H$ NMR (300 MHz, $d_6$-DMSO) δ 11.30 (br s, 1H), 7.49 (d. J=1.4 Hz, 1H), 7.43 (dd, J=8.2 Hz, 1H), 7.14 (d, J=8.2 Hz, 1H), 5.31 /(s, 1H), 2.20 (s, 3H), 2.22 (s, 3H), 2.08 (s, 3H); MS(ES) m/z 203 [M+H].

f) 1-(3,4-Dimethylphenyl)-3-methyl-5-oxo-3-pyrazolin-4-carbaldehyde

Phosphorus oxychloride (4.82 mL, 51.6 mmol) was added dropwise to an ice-cooled, stirred suspension of 1-(3,4-dimethylphenyl)-3-methyl-3-pyrazolin-5-one (8.70 g, 43.0 mmol) in dimethylformamide (18.0 mL) at such a rate as to maintain the temperature below 20° C. After the addition, the mixture was heated at 100° C. for 2 h, then cooled, poured into iced water (200 mL). The resulting mixture was stirred for 18 h, then filtered. The solid was washed with water and dried to give the title compound (7.83 g, 79%) as a cream-coloured powder. $^1H$ NMR (300 MHz, $d_6$-DMSO) δ 9.63 (s, 1H), 7.47 (s, 1H), 7.41 (d, J=8.1 Hz, 1H), 2.23 (d, J=8.2 Hz, 1H), 2.34 (s, 3H), 2.27 (s, 3H), 2.25 (s, 3H).

MS (ES) m/e 231 $[M+H]^+$.

g) 3'-{[1-(3,4-Dimethylphenyl)-3-methyl-5-oxo-1,5-dihydropyrazol-4-ylidenemethyl]amino}-2'-hydroxybiphenyl-3-carboxylic Acid A solution of 1-(3,4-dimethylphenyl)-3-methyl-5-oxo-3-pyrazolin-4-carbaldehyde (10 mg, 0.043 mmol) and 3'-amino-2'-hydroxybiphenyl-3-carboxylic acid hydrochloride (11 mg, 0.042 mmol) in ethanol (1 mL) was shaken with 0.2M aq. sodium acetate (0.25 mL, 0.05 mmol) for 1 h. 0.06M aq. hydrochloric acid (3 mL) was added and shaking continued for 1 h. The solid was filtered, washed with water and dried under reduced pressure to afford the title compound (14 mg, 74%) as a cream-coloured powder. $^1H$ NMR (300 MHz, $d_6$-DMSO) δ 13.08 (br s, 1H), 11.79 (d, J=13.8 Hz, 1H), 9.56 (s, 1H), 8.71 (d, J=13.2 Hz, 1H), 8.14 (s, 1H), 7.97 (d, J=7.8 Hz, 1H), 7.83–7.80 (m, 3H), 7.71 (d, J=8.2 Hz, 1H), 7.62 (t, J=7.8 Hz, 1H), 7.16–7.11 (m, 3H), 2.31 (s, 3H), 2.26 (s,3H), 2.22 (s, 3H).

Example 2—Capsule Composition

An oral dosage form for administering a presently invented agonist of the TPO receptor is produced by filing a standard two piece hard gelatin capsule with the ingredients in the proportions shown in Table I, below.

TABLE I

| INGREDIENTS | AMOUNTS |
|---|---|
| 3'-{[1-(3,4-Dimethylphenyl)-3-methyl-5-oxo-1,5-dihydropyrazol-4-ylidenemethyl]amino}-2'-hydroxybiphenyl-3-carboxylic acid (Compound of Example 1) | 25 mg |
| Lactose | 55 mg |
| Talc | 16 mg |
| Magnesium Stearate | 4 mg |

Example 3—Injectable Parenteral Composition

An injectable form for administering a presently invented agonist of the TPO receptor is produced by stirring 1.5% by weight of 3'-[1-(3,4-Dimethylphenyl)-3-methyl-5-oxo-1,5-dihydropyrazol-4-ylidenemethyl]amino)-2'-hydroxybiphenyl-3-carboxylic acid in 10% by volume propylene glycol in water.

Example 4—Tablet Composition

The sucrose, calcium sulfate dihydrate and a presently invented agonist of the TPO receptor, as shown in Table II below, are Nixed and granulated in the proportions shown with a 10% gelatin solution. The wet granules are screened, dried, mixed with the starch, talc and stearic acid, screened and compressed into a tablet.

TABLE II

| INGREDIENTS | AMOUNTS |
|---|---|
| 3'-{[1-(3,4-Dimethylphenyl)-3-methyl-5-oxo-1,5-dihydropyrazol-4-ylidenemethyl]amino}-2'-hydroxybiphenyl-3-carboxylic acid | 20 mg |
| calcium sulfate dihydrate | 30 mg |
| sucrose | 4 mg |
| starch | 2 mg |
| talc | 1 mg |
| stearic acid | 0.5 mg |

While the preferred embodiments of the invention are illustrated by the above, it is to be understood that the invention is not limited to the precise instructions herein disclosed and that the right to all modifications coming within the scope of the following claims is reserved.

What is claimed is:

1. A compound represented by the following Formula (I):

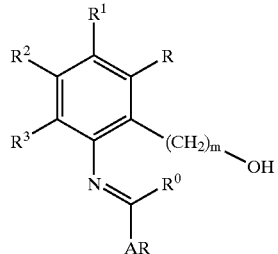

(I)

wherein:

R, $R^1$, $R^2$ and $R^3$ are each independently selected from hydrogen, $C_{1-6}$alkyl, $C_{1-6}$alkoxy, —$(CH_2)_pOR^4$, —$C(O)OR^4$, formyl, nitro, cyano, halogen, aryl, substituted aryl, substituted alkyl, —$S(O)_nR^4$, cycloalkyl, —$NR^5R^6$, protected —OH, —$CONR^5R^6$, phosphonic acid, sulfonic acid, phosphinic acid and —$SO_2NR^5R^6$, where p is 0–6, n is 0–2, $R^4$ is hydrogen, alkyl, cycloalkyl, $C_1$–$C_{12}$aryl, substituted alkyl, substituted cycloalkyl and substituted $C_1$—$C_{12}$aryl, and $R^5$ and $R^6$ are each independently selected from hydrogen, alkyl, substituted alkyl, $C_{3-6}$cycloalkyl, and aryl, or $R^5$ and $R^6$ taken together with the nitrogen to which they are attached represent a 5 to 6 member saturated ring containing up to one other heteroatom selected from oxygen and nitrogen;

$R^0$ is selected from hydrogen, $C_1$–$C_{10}$alkyl and substituted $C_1$–$C_{10}$;

m is 0–6; and

AR is a cyclic or polycyclic aromatic ring containing from 3 to 16 carbon atoms and optionally containing one or more heteroatoms, provided that when the number of carbon atoms is 3 the aromatic ring contains at least two heteroatoms and when the number of carbon atoms is 4 the aromatic ring contains at least one heteroatom, and optionally substituted with one or more substituents selected from the group consisting of: alkyl, substituted alkyl, aryl, substituted cycloalkyl, substituted aryl, aryloxy, oxo, hydroxy, alkoxy, cycloalkyl, acyloxy, amino, N-acylamino, nitro, cyano, halogen, —$C(O)OR^4$, —$C(O)NR^{10}R^{11}$, —$S(O)_2NR^{10}R^{11}$, —$S(O)_nR^4$ and protected —OH, where n is 0–2, $R^4$ is hydrogen, alkyl, cycloalkyl, $C_1$–$C_{12}$aryl, substituted alkyl, substituted cycloalkyl and substituted $C_1$–$C_{12}$aryl; and $R^{10}$ and $R^{11}$ are independently hydrogen, cycloalkyl, $C_1$–$C_{12}$aryl, substituted cycloalkyl, substituted $C_1$–$C_{12}$aryl, alkyl or alkyl substituted with one or more substituents selected from the group consisting of: alkoxy, acyloxy, aryloxy, amino, N-acylamino, oxo, hydroxy, —$C(O)OR^4$, —$S(O)_nR^4$, —$C(O)NR^4R^4$, —$C(O)_2NR^4R^4$, nitro, cyano, cycloalkyl, substituted cycloalkyl, halogen, aryl, substituted aryl and protected —OH, or $R^{10}$ and $R^{11}$ taken together with the nitrogen to which they are attached represent a 5 to 6 member saturated ring containing up to one other heteroatom selected from oxygen and nitrogen, where $R^4$ is as described above and n is 0–2;

and pharmaceutically acceptable salts, hydrates, solvates and esters thereof;

provided that at least one of R, $R^1$, $R^2$ and $R^3$ is a substituted aryl group.

2. A compound of claim 1 which is

3'-{[1-(3,4-Dimethylphenyl)-3-methyl-5-oxo-1,5-dihydropyrazol-4-ylidenemethyl]amino}-2'-hydroxybiphenyl-3-carboxylic acid;

or a pharmaceutically acceptable salt, hydrate, solvate or ester thereof.

3. A method of treating of thrombocytopenia in a mammal, including a human, in need thereof which comprises administering to such mammal a therapeutically effective amount of a compound of Formula (I), as described in claim 1.

4. The method of claim 3 wherein the compound is

3'-{[1-(3,4-Dimethylphenyl)-3-methyl-5-oxo-1,5-dihydropyrazol-4-ylidenemethyl]amino}-2'-hydroxybiphenyl-3-carboxylic acid;

or a pharmaceutically acceptable salt, hydrate, solvate or ester thereof.

5. A method of enhancing platelet production in a mammal, including a human, in need thereof which comprises administering to such mammal a therapeutically effective amount of a compound of claim 1.

6. The method of claim 5 wherein the compound is

3'-{[1-(3,4-Dimethylphenyl)-3-methyl-5-oxo-1,5-dihydropyrazol-4-ylidenemethyl]amino}-2'-hydroxybiphenyl-3-carboxylic acid;

or a pharmaceutically acceptable salt, hydrate, solvate or ester thereof.

7. A pharmaceutical composition which comprises a compound of claim 1 and a pharmaceutically acceptable carrier.

8. The method of claim 3 wherein the compound is administered orally.

9. The method of claim 3 wherein the compound is administered parenterally.

10. A process for preparing a pharmaceutical composition containing a pharmaceutically acceptable carrier or diluent and an effective amount of a compound of the Formula (I) as described in claim 1 and pharmaceutically acceptable salts, hydrates, solvates and esters thereof which process comprises bringing the compound of the Formula (I) into association with the pharmaceutically acceptable carrier or diluent.

* * * * *